United States Patent [19]

Liss et al.

[11] Patent Number: 4,844,075

[45] Date of Patent: * Jul. 4, 1989

[54] TRANSCRANIAL STIMULATION FOR THE TREATMENT OF CEREBRAL PALSY

[75] Inventors: Saul Liss; Bernard Liss, both of Glen Rock, N.J.

[73] Assignee: Pain Suppression Labs, Inc., Elmwood Park, N.J.

[*] Notice: The portion of the term of this patent subsequent to Dec. 24, 2002 has been disclaimed.

[21] Appl. No.: 860,745

[22] Filed: May 7, 1986

Related U.S. Application Data

[63] Continuation-in-part of Ser. No. 618,144, Jun. 7, 1984, Pat. No. 4,614,193, Continuation-in-part of Ser. No. 640,104, Aug. 13, 1984, Pat. No. 4,627,438, Continuation-in-part of Ser. No. 569,476, , Pat. No. 4,550,733.

[51] Int. Cl.$^4$ ............................................. A61N 1/32
[52] U.S. Cl. ................... 128/419 R; 128/421
[58] Field of Search ............. 128/419 R, 421–423

[56] References Cited

U.S. PATENT DOCUMENTS

| | | | |
|---|---|---|---|
| 3,640,284 | 2/1972 | DeLangis | 128/422 |
| 3,791,373 | 2/1974 | Winkler et al. | 128/422 |
| 3,902,502 | 9/1975 | Liss et al. | |
| 4,155,366 | 5/1979 | DiMucci | 128/421 |
| 4,503,863 | 3/1985 | Katims | 128/421 |
| 4,559,948 | 12/1985 | Liss et al. | 128/419 R |

OTHER PUBLICATIONS

Malden & Charash, "Transcranial Stimulation for the Inhibition of Primitive Reflexes in Children with Cerebral Palsy" Neurology Report Spring 1985.

Okoye & Malden, "Use of Neurotransmitter Modulation to Facilitate Sensory Integration," Neurology Report, Fall 1986.

Primary Examiner—Ruth S. Smith
Attorney, Agent, or Firm—Hopgood, Calimafde, Kalil, Blaustein & Judlowe

[57] ABSTRACT

Cerebral palsy treatment apparatus and methodology employs a transcutaneous electronic wave to suppress pain and increase motor function. A first positive contact electrode is placed at the right side of the cranium, and a second negative contact electrode is placed at the left side of the cranium of the head. An electronic current wave comprising relatively high frequency pulses with a low frequency amplitude modulation is then applied between the first to the second electrodes.

4 Claims, 14 Drawing Sheets

TRANSCRANIAL STIMULATION FOR THE TREATMENT OF CEREBRAL PALSY

This application is a continuation-in-part of the following applications: (1) Ser. No. 618,144 filed on June 7, 1984, now U.S. Pat. No. 4,614,193; and (2) Ser. No. 640,104 filed on Aug. 13, 1984, now U.S. Pat. No. 4,627,438, which applications (1) and (2) are continuations-in-part of Ser. No. 569,476, now U.S. Pat. No. 4,550,733.

DISCLOSURE OF THE INVENTION

This invention relates to electronic pain suppression and spasticity reduction apparatus and methodology and, more specifically, to cerebral palsy treatment apparatus and procedure for treating symptoms incident to the disease.

Apparatus for electronic treatment of patients with cerebral palsy is known. See U.S. Pat. No. 4,559,998.

It is an object of the present invention to provide improved cerebral palsy treatment methodology; and more specifically, to treat patients of cerebral palsy by means of electronic transcranial stimulation in a safe, efficient and rapid manner to increase motor function and alleviate the pain and discomfort associated with the disease.

The above and other objects and features of the instant invention are realized in a specific illustrative cerebral palsy treatment apparatus and methodology which employs a transcutaneous electronic wave to suppress perceived pain and reduce spasticity as well as all other symptoms associated with cerebral palsy. A first positive contact electrode is placed at one side of the head of the patient, and a second negative contact electrode is placed at the opposite side of the patient's head. Preferably, the first and second electrodes are respectively placed between the ear and temple on the right and left sides of the patient's head. Advantageously, the first positive contact electrode may be placed on the right side of the cranium if the patient is right-handed, with the second negative contact electrode placed on the left side of the cranium. If the patient is left-handed, then the positions of the electrodes may be reversed: the first positive contact electrode may be placed on the left side of the cranium and the second negative contact electrode may be placed on the right side of the cranium. An electronic current wave comprising relatively high frequency pulses with a low frequency modulation is then applied from the first to the second electrodes.

The above and other features and advantages of the instant invention will become more clear from the following detailed description of a specific illustrative embodiment thereof, presented hereinbelow in conjunction with the accompanying drawings in which.

Cerebral palsy may be defined as a disability resulting from damage to the brain before, during or after birth which is outwardly manifested by muscular incoordination and speech disturbances. Prenatal injury may be caused by a variety of factors, including diabetes, encephalocele, erythroblastosis, hydrocephalus, microcephaly, rubella, toxemia, toxoplasmosis or heredity. Postnatal injury may result from concussions, encephalitis, infection, lead poisoning, sickle cell, trauma, tumor or other causes. Most often, however, the damage which causes cerebral palsy occurs at birth; those cases are the result of anoxia, breech birth, dystocia, prematurity, respiratory distress or other causes. See O'Reilly, D. E.; Walentynowic, J. E.; Etiological Factors in Cerebral Palsy: An Historical Review, *Develop. Med. Child Neurol.* 1981; 23: 633–642.

The apparatus of the instant invention has been found to relieve the symptoms of cerebral palsy in all subjects and to produce dramatic results with a relatively low level current and without chemical intervention.

Figure 1:
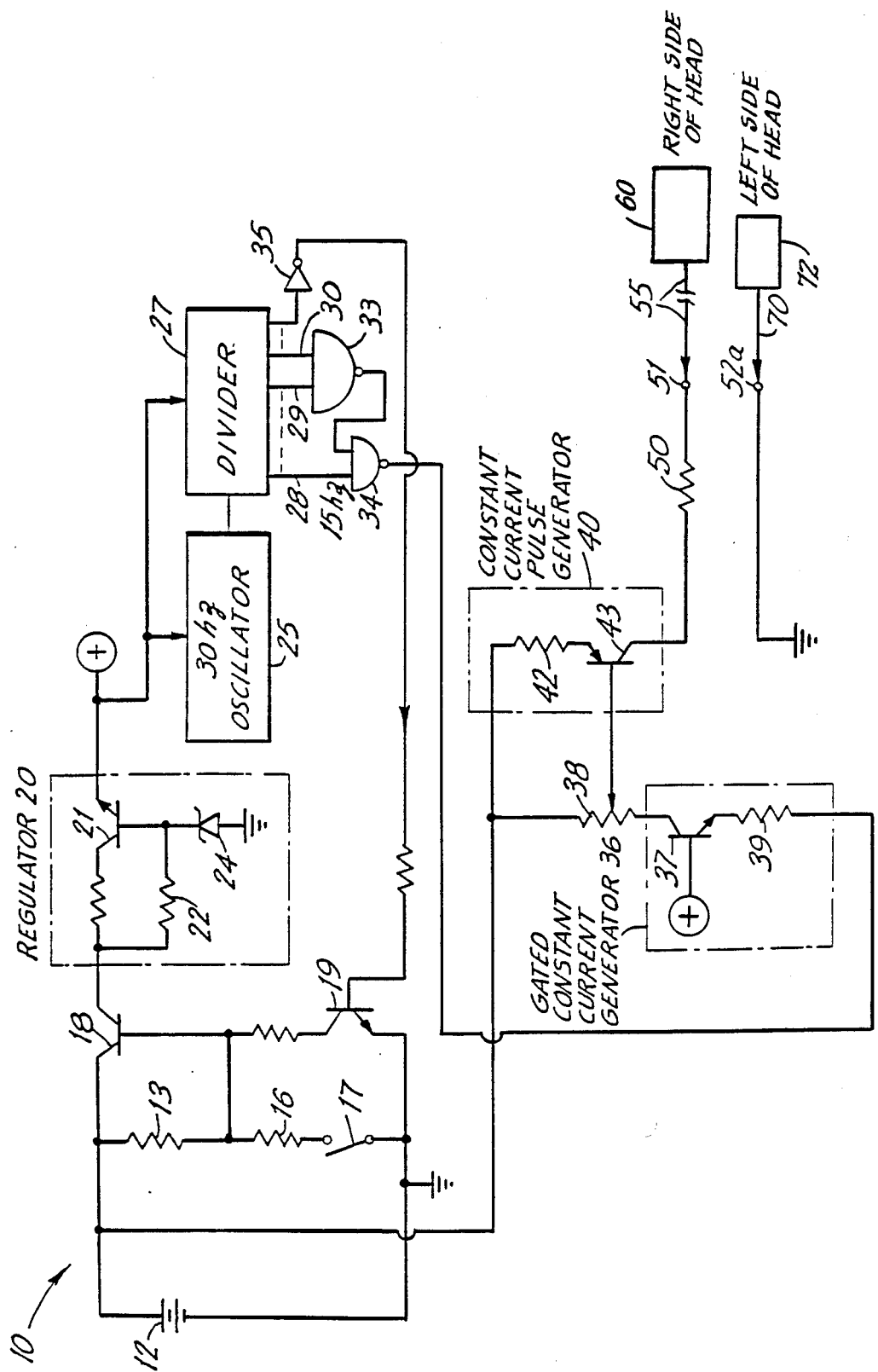
FIG. 1 is a schematic diagram of electronic cerebral palsy treatment apparatus embodying the principles of the present invention.

To illustrate performance of the instant invention in overview, the apparatus of FIG. 1 is utilized to treat the symptoms associated with the diseased state of a patient who is suffering from cerebral palsy. A first positive contact electrode 60 (FIG. 1) is placed on the right side of the cranium. A second negative contact electrode 72 (FIG. 1) is placed on the left side of the cranium. The treatments should be for 10–20 minutes, preferably 10 minutes.

An electronic wave (depicted in FIG. 2D) is applied between the first electrode 60, and the electrode 72 which are connected on common. The wave form of FIG. 2D comprises a low level (less than 4 milliamperes) pulse train of relatively high frequency, e.g., between 12 and 20 khz modulated in amplitude by a relatively low frequency wave in the range of 8 to 20 hz. The low frequency wave is preferably non-symmetrical (that shown in FIG. 2D), for example characterized by a 3:1 duty cycle, being on three quarters of the time and off one quarter of the recurring period. For concreteness only and without limitation, it will hereinafter be assumed that the high frequency pulse occurs at a 15 khz rate and 1–1.5 m.a. level, while being subject to a 15 hz modulation with a 3:1 duty factor.

Figure 2:
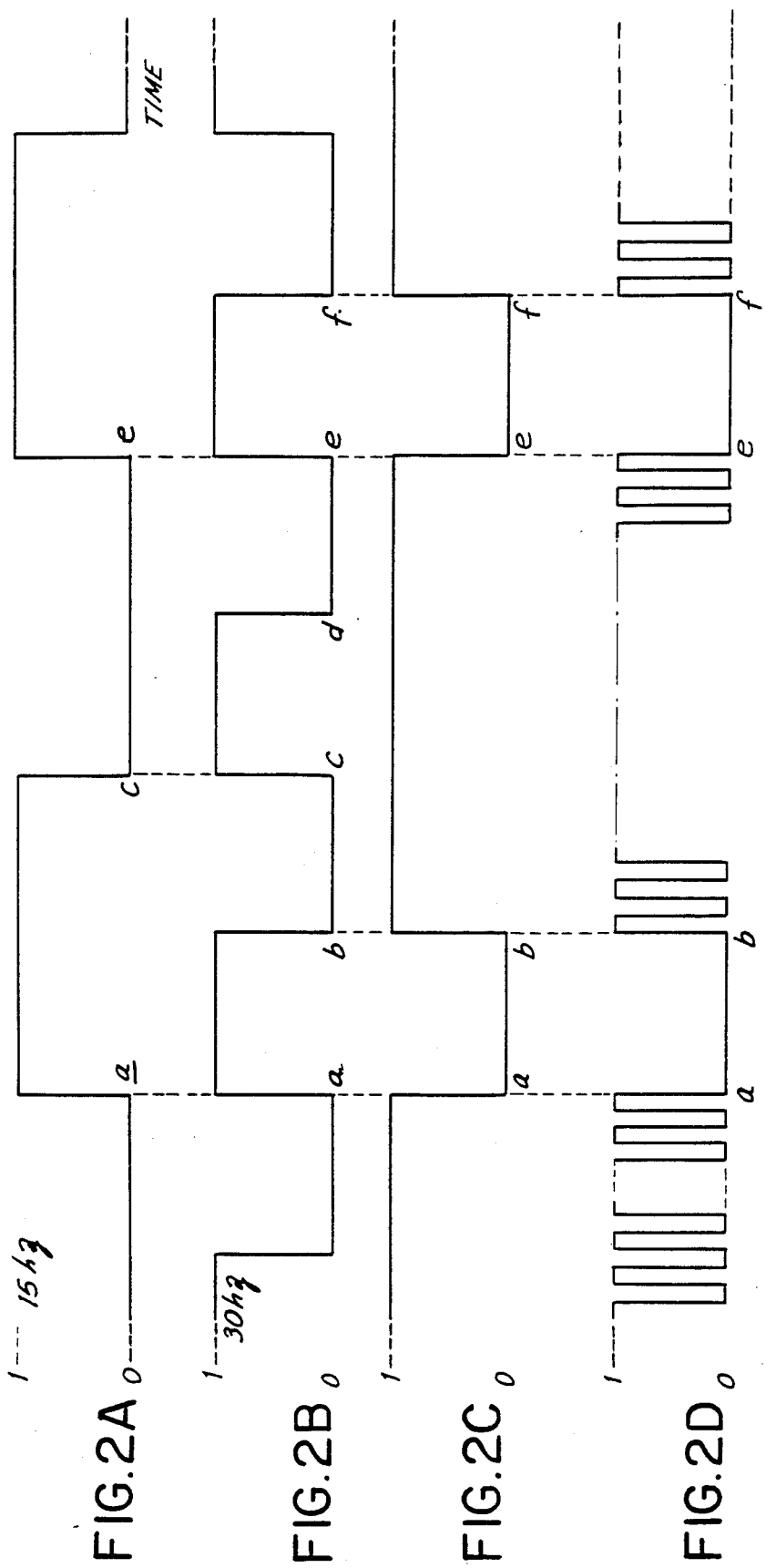
FIGS. 2A through 2D are wave forms illustrating the operation of the FIG. 1 apparatus.

It have found that the wave of FIG. 2D is effective to block the pain perceived and relieve the symptoms associated with cerebral palsy. One can see a gradual increase in the patient's motor function which is accompanied by alleviation of pain.

The particular mechanism causing elimination of the symptoms of cerebral palsy is believed to follow from some increase in neural transmission to the muscles which is responsive to the low frequency modulation envelope introduced into the body, with the high frequency wave constituent serving as a transcutaneous carrier for the low frequency modulation, thereby increasing coordination and motor function.

While the precise operative mechanism may be the subject of debate, the fact of the relief of pain, reduction of spasticity, and increase in coordination is not.

The FIG. 1 electronic apparatus 10 for generating and applying the wave form of FIG. 2D will now be specifically considered. A battery 12 is connected to a PNP series pass transistor 18 which, in turn, selectively passes the voltage from battery 12 through a voltage regulator 20 to form the positive direct current voltage supply for the apparatus 10 electronics. The unit is first turned on by momentarily closing a power-on switch 17. This applies a low voltage to the base of PNP transistor 18, turning that device on and effectively coupling the potential of battery 12 to a series pass transistor 21 in the voltage regulator 20. Because the final output of a counter or divider chain 27 is initially low on power turn on, the resulting high output of inverter 35 applies a high potential to the base of transistor 19, turning it on and thereby latching PNP transistor 18 to its conductive condition when switch 17 is released. This maintains the electronic apparatus on for a desired period which is determined by the frequency of an oscillator 25 and the division factor of the divider 27, i.e., the period required for the most significant stage of the counter 27 to reach its high or binary "1" state. The switched power supply assures that the electronic apparatus is not inadvertently left on to unduly discharge the battery 12.

The regulated output of battery 12 applied through PNP transistor 18 is converted to a lower regulated value by the regulator 20. Regulator 20 is per se well known and includes the series pass PNP transistor 21 having a constant voltage applied to the base thereof by a Zener diode 24 energized by a resistor 22. The constant potential output of regulator 20, which serves as the supply voltage for much of the remaining electronics of FIG. 1, is the characteristic reverse excitation voltage of Zener diode 24 less about 7/10 of a volt for the base-emitter drop of transistor 21.

As above noted, the active power supply interval for circuit 10 of the drawing is fixed and preset to a specific period. The above-discussed time out circuitry is employed to assure that the unit is not inadvertently left on. Many ways of achieving this result will be readily apparent to those skilled in the art. For example, a variable time out may be provided by employing a switch to connect the input of inverter 35 to varying ones of the more significant stage outputs of the pulse counter chain 27. Yet further, separate electronic or electromechanical timer apparatus, fixed or variable, all per se well known, may be employed to supply a positive potential to the base of transistor 19 for the desired "on" period; and to switch off the base drive to transistor 19, thereby turning off series pass transistor 18, when the desired operative period has passed.

A time base oscillator 25 supplies an input to the pulse counter or divider chain 27. The frequency of oscillator 25 is chosen for convenience to be an integral multiple of the pulse frequency (FIG. 2D) desired for delivery to the patient. For the assumed 15 khz desired frequency, a 30 khz oscillation repetition rate may be usefully employed for oscillator 25, such that the 15 khz signal is derived at a divide-by-two tap 28 of divider chain 27. The 15 khz signal is supplied as one input to a NAND gate 34, the output of which corresponds to the ultimately desired wave of FIG. 2D. Outputs 29 and 30 of divider 27 are supplied as inputs to a NAND gate 33, the output of which is supplied as a second input to the NAND gate 34. The output 29 of divider 27 supplies the 30 hz wave of FIG. 2B (pulse division factor 1,000 at tap 29), while the 15 hz wave of FIG. 2A is supplied at a divider output 30 (divider factor: 2,000). Logic gate 33 generates the output wave of FIG. 2C, being at its high or Boolean "1" value when either of the waves of FIG. 2A or 2B is low (i.e., preceding the time a, during the interval b-e,—and following time f). Correspondingly, during the periods a-b and e-f when the output at divider 27 taps 29 and 30 are both high, the output of gate 33 is low (Boolean "0" value).

The wave form of FIG. 2C is supplied as one input to the gate 34 together with the 15 khz pulse train at the divide-by-two counter 27 output port 28. Accordingly, the output of NAND gate 34 switches between its high and low state during the periods when the FIG. 2C wave is high, i.e., preceding time a, during the interval b-e, following the time f, and so forth for the recurring pattern illustrated by FIGS. 2A-2D.

The voltage wave form of FIG. 2D is converted to a current in the milliampere range for application to the patient by the following circuitry of FIG. 1. As a first matter, a gated constant current generator 36 passes a gated current (either off or of a fixed value) through a potentiometer 38 under control of the output of the NAND gate 34. When the output of NAND gate is low, a transistor 37 in constant current generator 36 is on and a current substantially given by the positive potential output of regulator 20 (applied to the base of transistor 37) less a 7/10 of a volt base emitter drop for the transistor 37, divided by the resistance value of the resistance 39 in the emitter circuit of transistor 37. The voltage at the variable tap of the potentiometer 38 is supplied to the base of a PNP transistor 43 of a constant current pulse generator 40. The output of pulse generator 40 is a current which switches between its off (zero current) state, and a value given by the voltage at the potentiometer 38 tap, less a diode drop for the emitter-base of transistor 43, divided by the resistance value of resistor 42 connected in the emitter circuit of the PNP device 43. This pulsed current output of pulse generator 40 corresponds in wave form to FIG. 2D, and is at a level, determined by the setting of potentiometer 38, in the low milliampere range. It is this current pulse which is ultimately delivered to the patient to provide the requisite relief of symptoms.

In a typical application the patient is provided with the potentiometer 38. The potentiometer is first turned up so that the administered current pulses provide a noticeable tingling sensation on the patient's skin surface. The patient is then instructed to turn down the potentiometer adjustment until the sensation just disappears. This will provide the amount of transcutaneous electronic stimulation to treat the symptoms associated with the patient's disease. The potentiometer setting may be adjusted by the patient as required.

The current pulses from generator 40 pass through a protective, series limiting resistor 50 to an output terminal 51. It there flows via the lead 55 connected to terminal 51 to the electrode 60 adhered to the right side of the cranium. The current transcutaneously passes into the patient, flows through the patient, and returns to electronic ground via the electrode pad 72 adhered to the left side of the cranium. Electrode 72 is connected to electronic system ground via lead 70 and apparatus terminal port 52a.

As above noted, the apparatus and methodology of the instant invention treats the symptoms associated with cerebral palsy. The apparatus and methodology has manifest advantages for alleviating the patient's symptoms.

In one application of the invention, for example, tests performed showed that the treatment of patients with spastic cerebral palsy with the inventive transcranial stimulation in addition to physical therapy is superior to conventional treatment offered alone. In the following tests, for example, all of the subjects were children who suffered anoxia perinatally; four were premature ranging in gestational age from 27 to 30 weeks and weights from 2 pounds 2 ounces to 4 pounds; two had postnatal anoxia due to blood platelet formation; one child was anoxic as a result of a spontaneous, rapid vaginal delivery following a placenta praevia; the remaining thirteen were anoxic at birth because of trauma caused by postmaturity, prolonged labor or simply because the baby was large and the umbilical cord was compressed during delivery.

The spasticity which results from the birth anoxia is usually evident at about eleven to twelve weeks after delivery. As the normal child begins to integrate the primitive reflexes with which all infants were born, the spastic child does not. His brain does not pass through the normal milestones of development because these early, normal reflexes have persisted and become pathological. All of the human neural pathways are present in his brain but are unable to function. Each milestone depends upon that which precedes it. The neural axons which bud and branch with each new knowledge, are the basic building blocks upon which the next developmental level is based.

The treatment techniques utilized with the subjects of this application of the invention were physiologically appropriate developmental sequences which encompass many techniques. The techniques were applied electrically, and were selected from such sources as Rood and Bobath. The same techniques were employed with each of the children prior to and during the time of the research project.

Transcranial stimulation seemed to inhibit primitive motor reflexes when they persisted past the normal integration time in the brain. With the suppression of those now abnormal reflexes, the subjects were more able to be trained in normal developmental patterns through the application of the developmental physical, occupational and speech therapy techniques. Most importantly, those patterns of movement have persisted. It is postulated that the mechanism by which this process occurred was through axon-budding in a conducive biochemical environment. It is hypothesized that the conversion of tryptophan to serotonin provides this enhanced environment. Such an hypothesis is supported by tests on previous patients pre and post stimulation.

As a result of a successful initial evaluation of the Neurotransmitter Modulator (NTM) as an electrical means of reducing spasticity in 19 children with spastic cerebral palsy the present experiments were planned.

Evaluation Methods

The Malden Gross Motor Rating Scaes I (Table 1), II (Table 2), and III (Table 3) were developed and used as a set of tools for assessing capability levels. These scales, together with the Advanced Gross motor Skills Scale (Table 4), constitute a total gross motor picture of the child (on a total combined scale of 200 points), which is easily programmed into a computer for future reference.

The scales also facilitate the therapist's explanations to parents and to other medical personnel. The use of color on the rating sheets indicates quality of the activity, i.e., red indicates less than normal performance; yellow indicates use of appropriate body parts without total integration. For example, a child may roll from his abdomen to his back using an extensor thrust instead of segmentation of his body. This rating would be 2 yellow. As he begins to use segmental movement, the rating would be 2 red and finally with integration, simply 2.

The rating points in Rating Scale I (Table 1) assigned through "bipedal stand", are the same for all children. If, because of lack of head and/or trunk control, the child is unable to ambulate without supportive equipment, Rating Scale III (Table 3) should be used for the remaining activities. If none of the supportive measures are necessary Rating Scale II (Table 2) is continued. In Rating Scale IV (Table 4) rating points and letters are assigned to advanced gross motor skills.

Research Methods

Twenty children with spastic cerebral palsy, ranging from 2.5 months to 15 years, 5 months of age, were selected for three months of transcranial stimulation with the NeuroTransmitter Modulator (NTM) (Model GL 105C, manufactured by Pain Suppression Labs, Inc., Wayne, N.J.) in addition to their usual therapy programs.

The children selected represent a cross-section of a seventy patient per week private practice in a middle class suburban community. The children had at least normal intelligence. The extent of the spasticity varied from mild to severe. Those involved included eight spastic quadriplegias, eight spastic hemiplegias and four diplegias. Some of the children had additional neurological deficits but their primary problem was spasticity.

Each patient was to have six weeks of treatment as follows:
(a) Ten patients with ten minutes transcranial treatment, twice daily using an active NTM.
(b) Ten patients with ten minutes transcranial treatment, twice daily using a placeo NTM.
(c) Those who started with active NTM had a placebo unit for an additional six weeks.
(d) Those who started with a placebo (placebo instrument is active for first 70 seconds during which time the unit is adjusted to turn to subthreshold for the perception of sensation, whereupon it automatically turns itself off) NTM had an active unit for an additional six weeks.

The study was double blind in nature; neither the subject, his parents nor his therapist(s) were cognizant of the status of the unit, i.e., whether it was an active or a placebo unit.

Each child was given a test unit. Release forms were signed by one parent of each child, for use of the unit. Instruction in the use of the unit was explained and demonstrated and written instructions were furnished. A urine specimen was taken by the parent once weekly and sent to a hospital laboratory for analysis of tryptophan and serotonin content.

All subjects were graded using the Malden Gross Motor Scales which utilizes numerical values for milestones and color for milestones quality as previously described. These values were formulated to facilitate rating and for ease in computer programming. Reflexes were tested prior to stimulation with the unit and then again 35 minutes after the ten minute stimulation treatment.

Results

Figure 3:
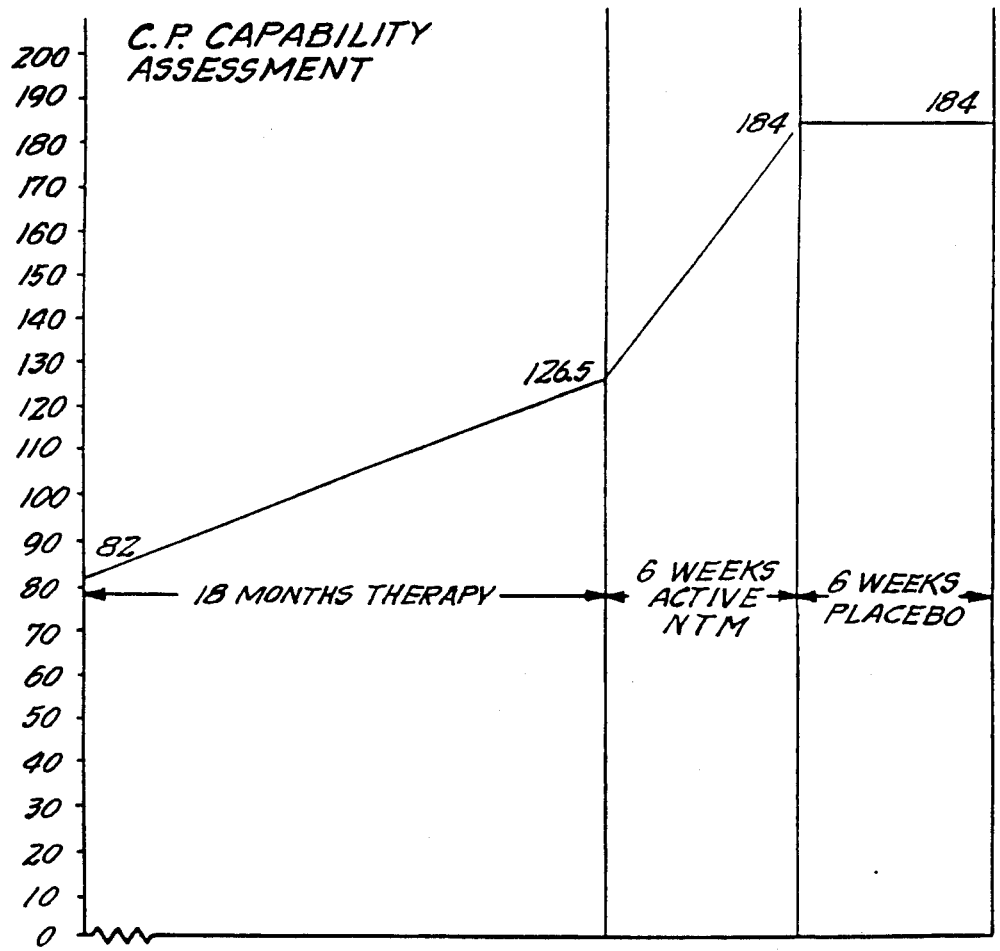
FIG. 3 is a graph showing cerebral palsy capability assessment for a subject who was in group A (Active/Placebo).

The most dramatic results of the study were obtained on subject number 1 who was in a Group A (Active/Placebo). The 15.5 year old child had an assessment improvement of 44.5 points during 18 months of conventional therapy. During six weeks of active NTM treatment in conjunction with physical therapy he gained 57.5 additional points. Following an additional six weeks of placebo treatment he did not gain any further assessment points (FIG. 3). It is interesting to note that he was receiving physical therapy during the placebo period with no apparent effect.

Figure 4:
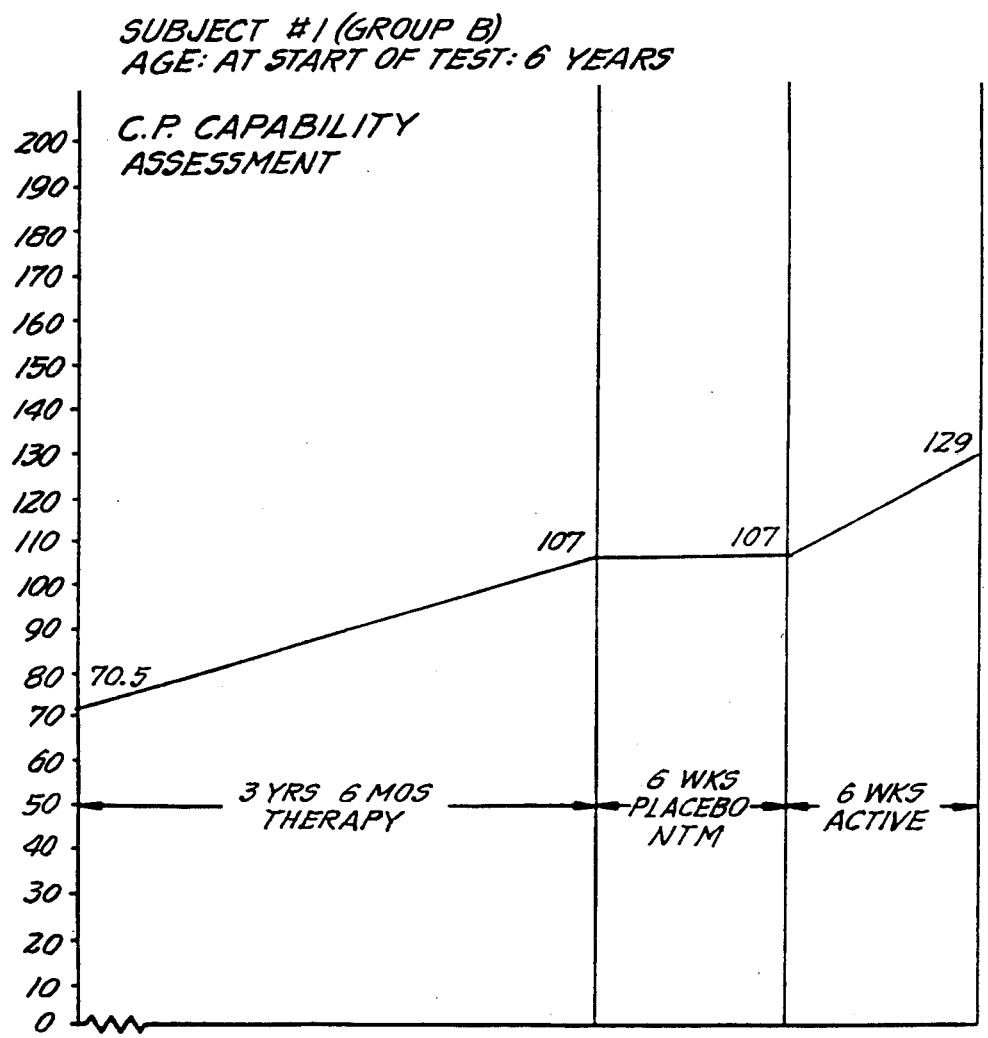
FIG. 4 is a graph showing cerebral palsy capability assessment for a subject who was in group B (Placebo/Active).

Subject number 3, a six year old child who was in Group B (Placebo/Active) showed a similar result, i.e., a sharp gain during the active period with no gain during the placebo period (FIG. 4).

Figure 5:
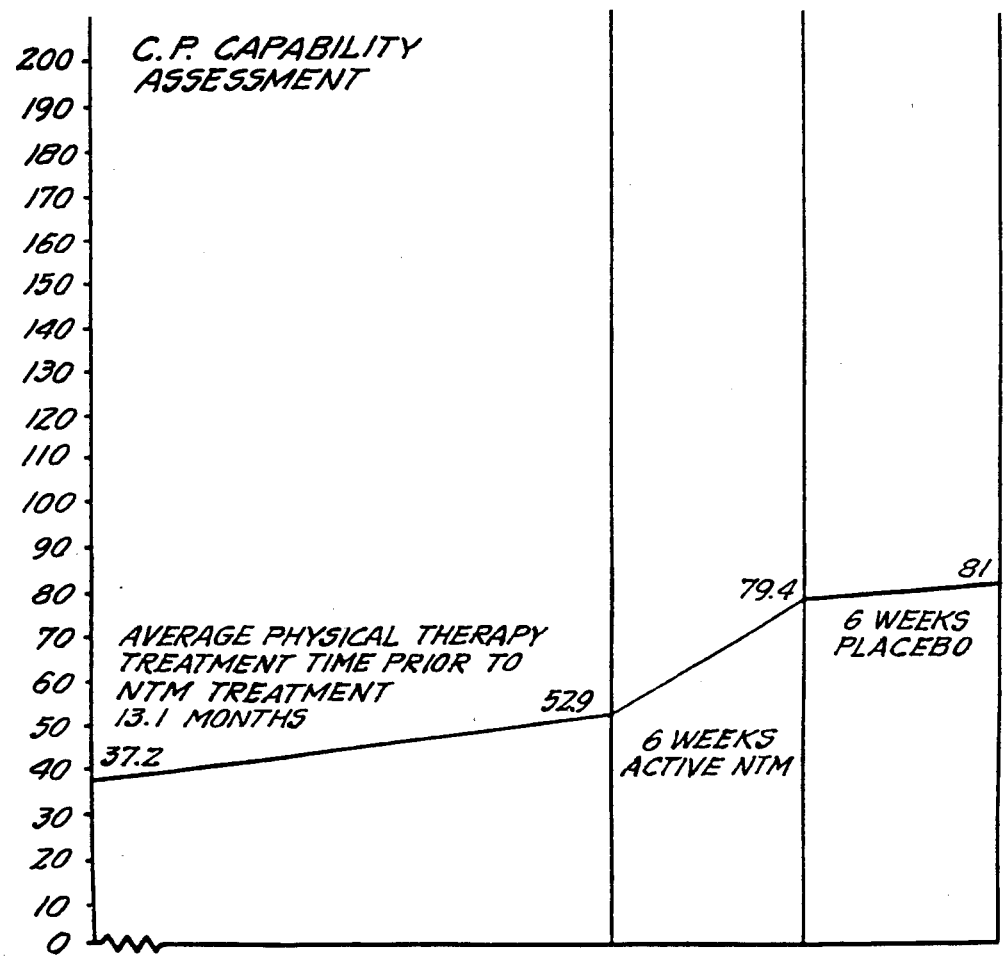
FIG. 5 is a graph showing cerebral palsy capability assessment for 10 patients, averaged, given active treatment followed by placebo treatment.

A comparison of the average gains of Group A and Group B yields some interesting figures. In the first 13.1 months of conventional treatment the subjects in Group A gained 15.7 assessment points. During the six weeks of active NTM treatment the subjects averaged a 26.5 gain in points. During the six week placebo period there was an average gain of 1.6 points by the group (FIG. 5).

Figure 6:
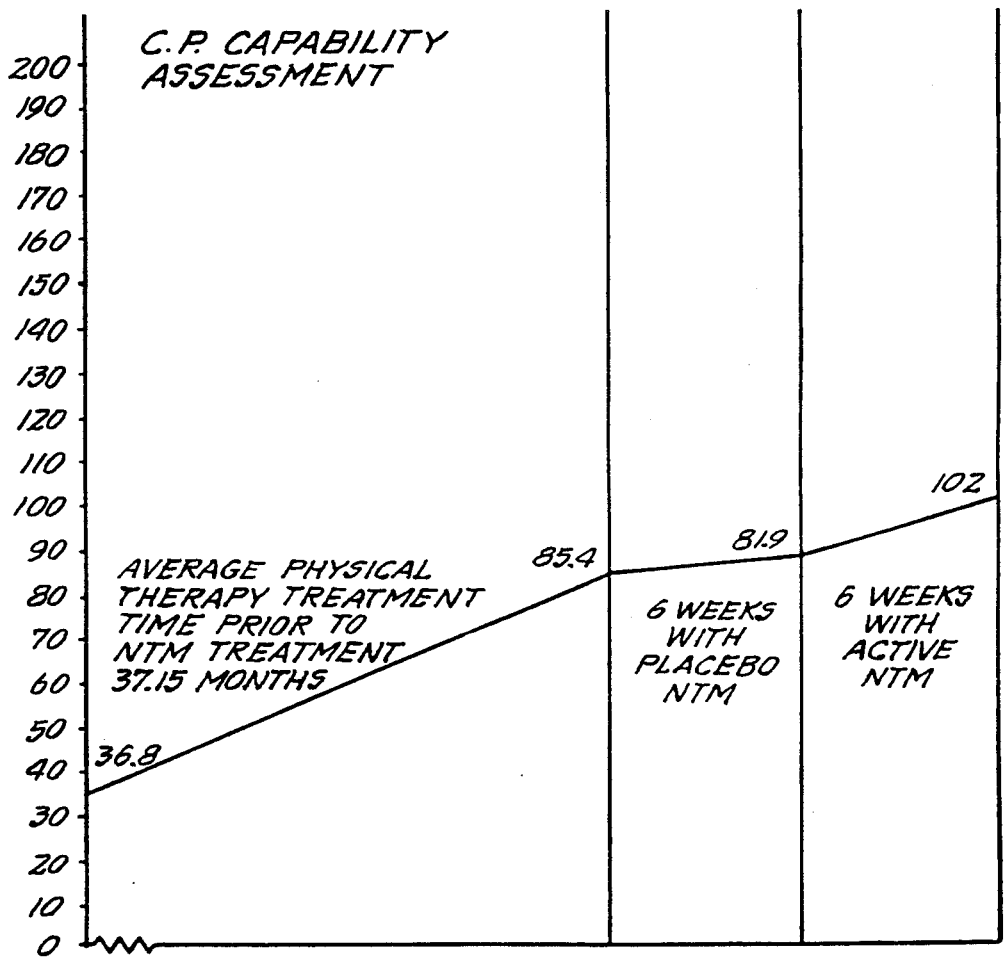
FIG. 6 is a graph showing cerebral palsy capability assessment for 6 patients, averaged, given placebo treatment followed by active treatment.

The six subjects in Group B who completed all treatments had an average gain of 48.6 assessment points during the 31.15 months of conventional physical therapy prior to experimental treatment. During the six weeks of active NTM treatment the subjects had an average gain of 14.1 points (FIG. 6).

It is interesting to note that the subjects in Group A had a combined gain of 28.1 points during the NTM active/placebo period while the subjects in Group B had a combined gain of 16.6 points.

Statistical analysis was performed utilizing a two tailed student's T test. The mean improvement of 26.5 points for Group A with active treatment was significant at the 0.01 level when compared to the mean value of 1.6 points during the placebo period.

The mean value of 2.5 points for Group B during the placebo period was not statistically significant when compared to the mean gain of 14.1 points during the active treatment. When subject number 10, who had a large gain during the placebo period, is removed from analysis, the results for remaining subjects become statistically significant at the 0.05 level. While applicants understand that subjects cannot be removed legitimately from data analysis, it is interesting to do so in this case to speculate on possible reasons that one subject skewed the data.

Before beginning the three months in the research project, the researchers tested the units on 19 of the 20 participants in this experiment to see if it was worth the time involved to complete a fully developed study. This approach made it difficult for the parents and the therapists to distinguish between the active and the placebo units.

Advancement during the placebo period of the subject number 10 may very well have occurred because of the carryover effect of the pretest treatment plus physical therapy.

Individual data on all subjects in this study are found in Tables 5 and 6.

Conclusions

Figure 7:
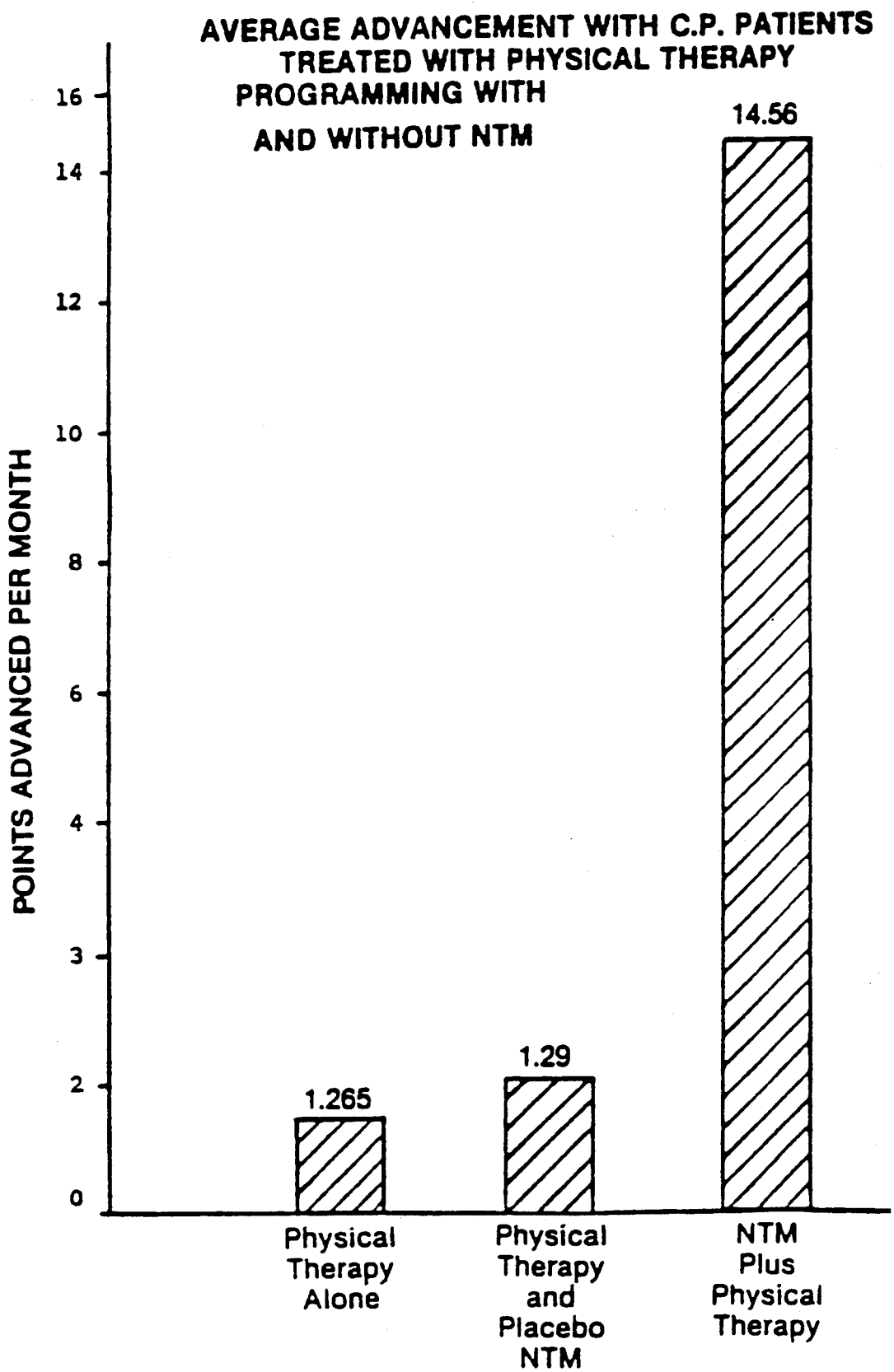
FIG. 7 is a graph showing average advancement with cerebral palsy patients treated with physical therapy programming with and without active treatment.

The results of this double blind study, depicted in FIG. 7, are highly significant ($P<0.001$) and would seem to indicate that the treatment of children with spastic cerebral palsy with NTM in addition to physical therapy is superior to conventional treatment offered along. Placebo treatments have little further effect on conventional treatment.

In another application of the invention, the apparatus and methodology of the instant invention may also be used to treat brain-damaged children with minimal cerebral dysfunction (learning disabilities), by increasing graphomotor functions, visuospatial perception, and fine motor coordination. Cerebral palsy patients with severe spasticity and visual perception difficulties, as well as those with moderate spasticity can be treated with the apparatus and methodology of the invention.

The rate of improvement of trunkal stability, daily living skills, and had function among persons with spasticity were compared, given the following experimental conditions:
(1) No therapeutic intervention;
(2) Physical therapy with transcranial stimulation;
(3) Occupational and physical therapy with transcranial stimulation.

Subjects were chosen among persons who are not currently receiving transcranial stimulation. Subjects range in age from five years upward, and were diagnosed as having spasticity in addition to other physical and/or mental disabilities. Only subjects having attained a motor age of at least nine months were included . . . i.e., they are able to roll over independently, sit when propped, maintain quadruped when placed, etc. Only subjects having superior through educable levels of intelligence were included.

Each subject's medical profile were reviewed to determine both the nature and severity of the handicapping condition. Factors regarding the age, degree of spasticity, motor maturity/degree of involvement, and intelligence were reviewed. Following review of each medical profile, the subjects were assigned in an ordinal manner to one of the three experimental groups (i.e., the first subject whose primary limiting factor is spasticity was assigned to group #1, the second subject whose primary limiting factors is spasticity was assigned to group #2, etc.).

Figure 8:
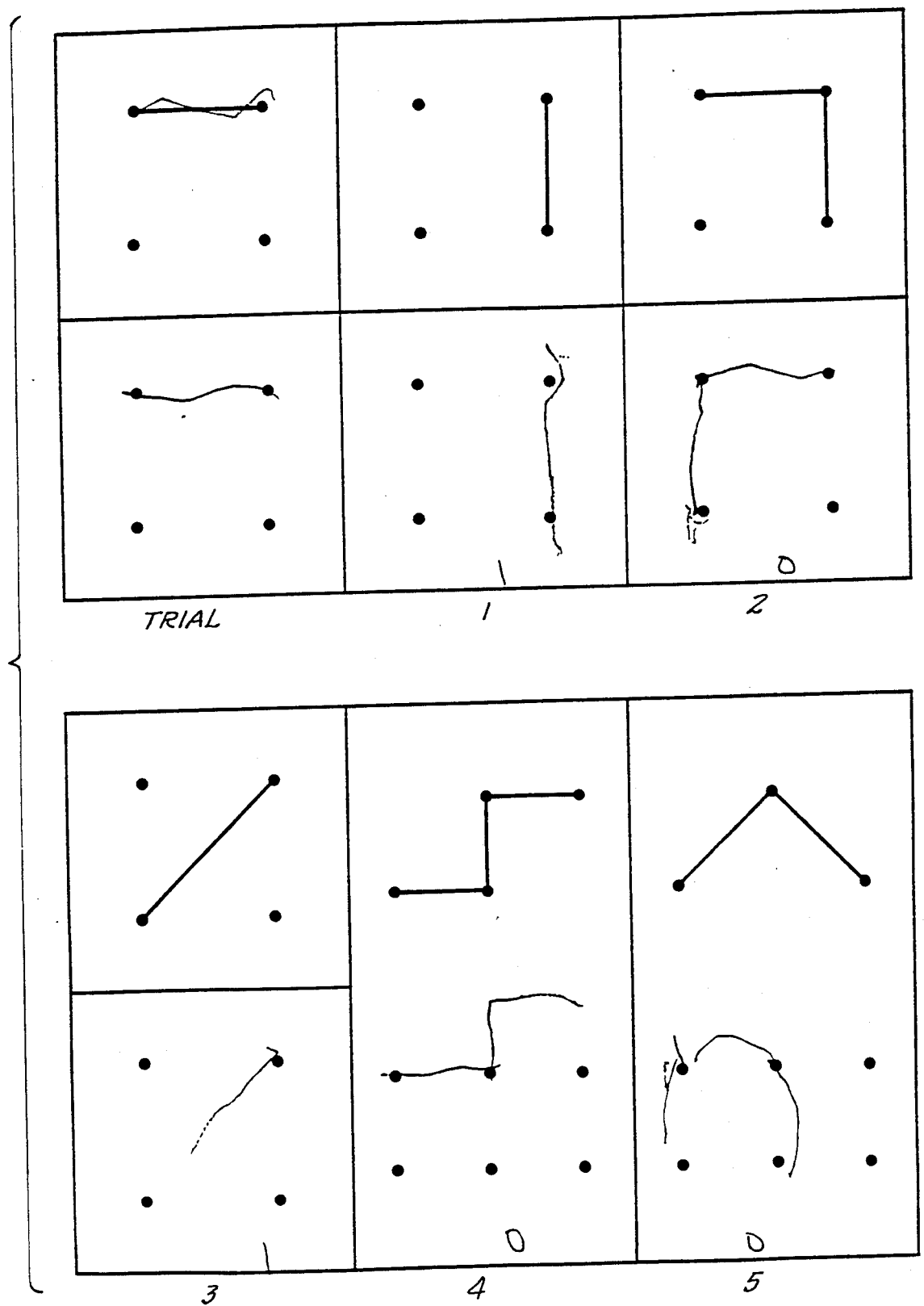
FIGS. 8–11 represent design copying tests, i.e., standardized test instrument measurements used to evaluate eye-hand coordination and spatial perception.
Figure 10:
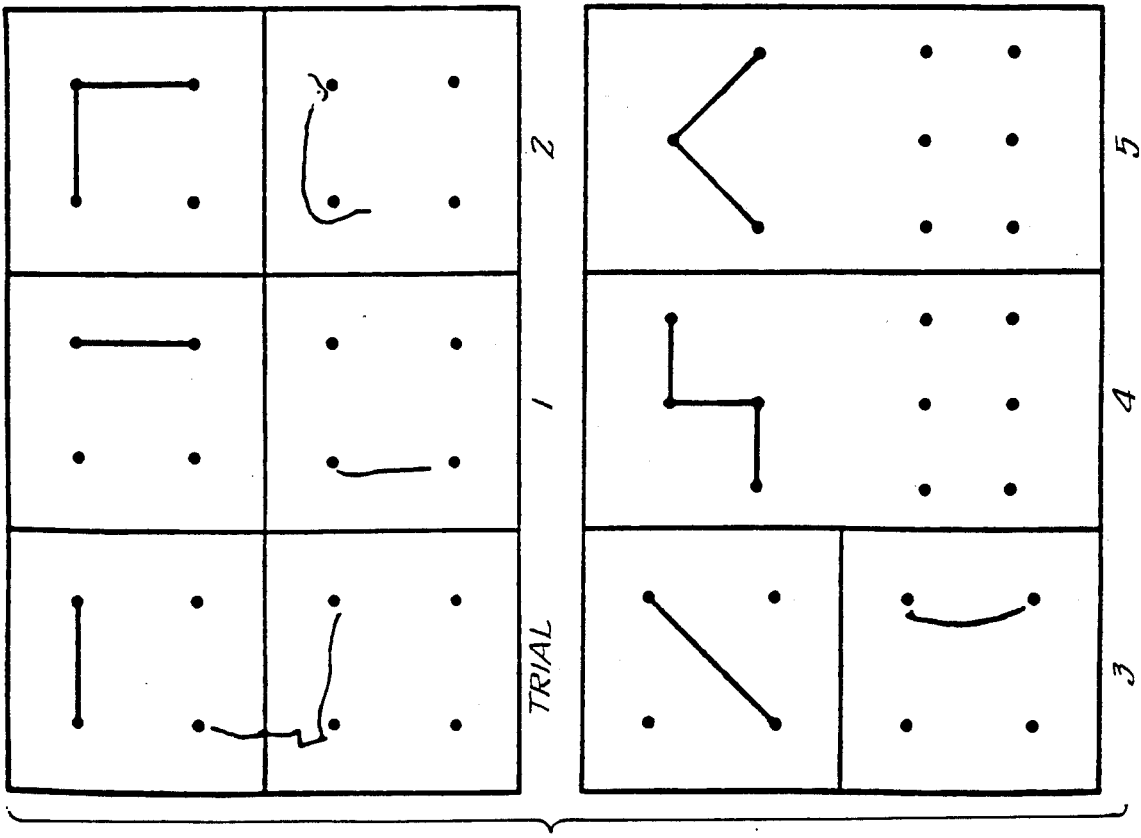
Figure 12:
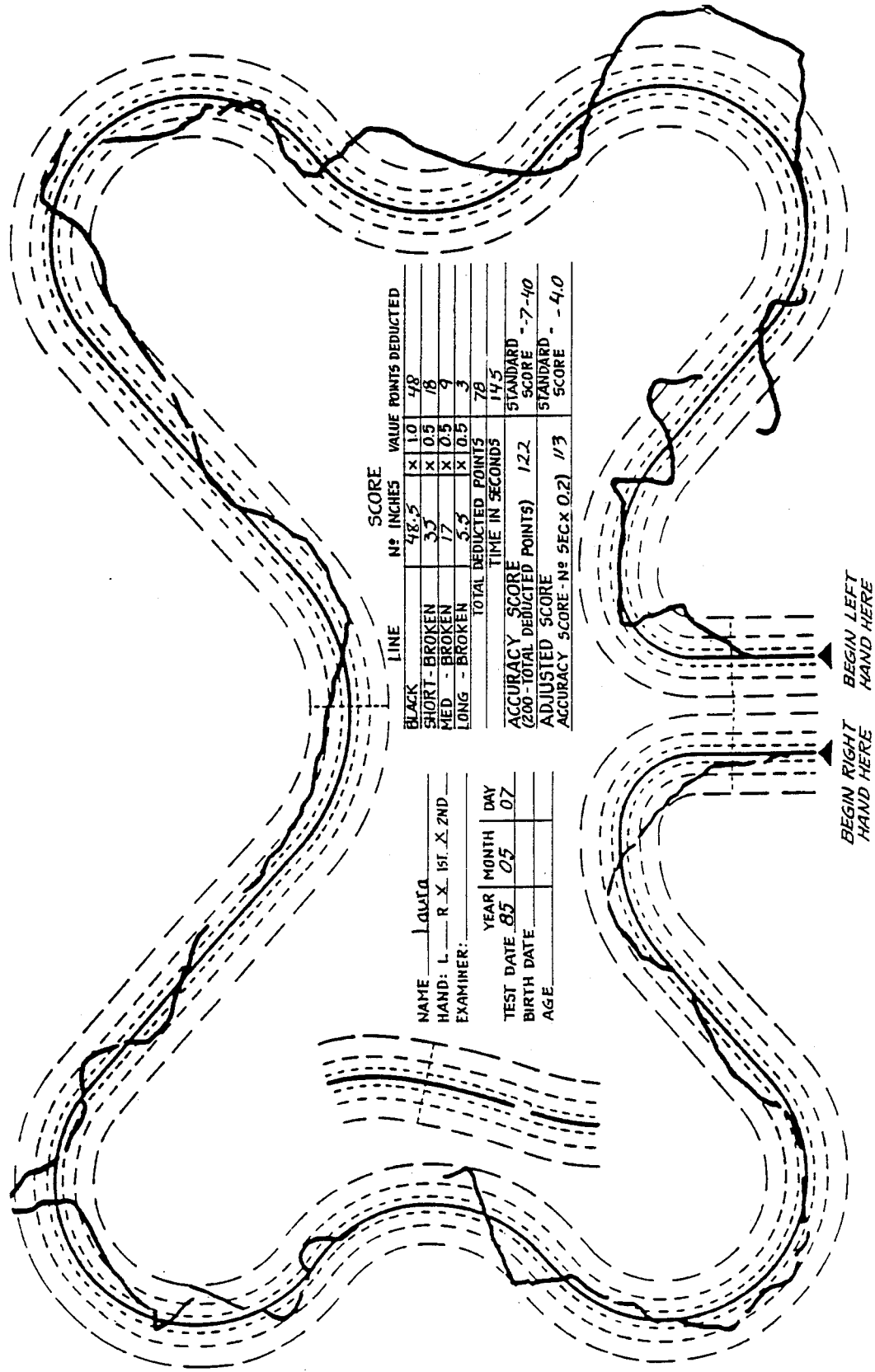
FIGS. 12–15 represent motor accuracy tests, i.e., standardized test instrument measurements designed to evaluate the quality of paper and pencil type activities.
Figure 14:
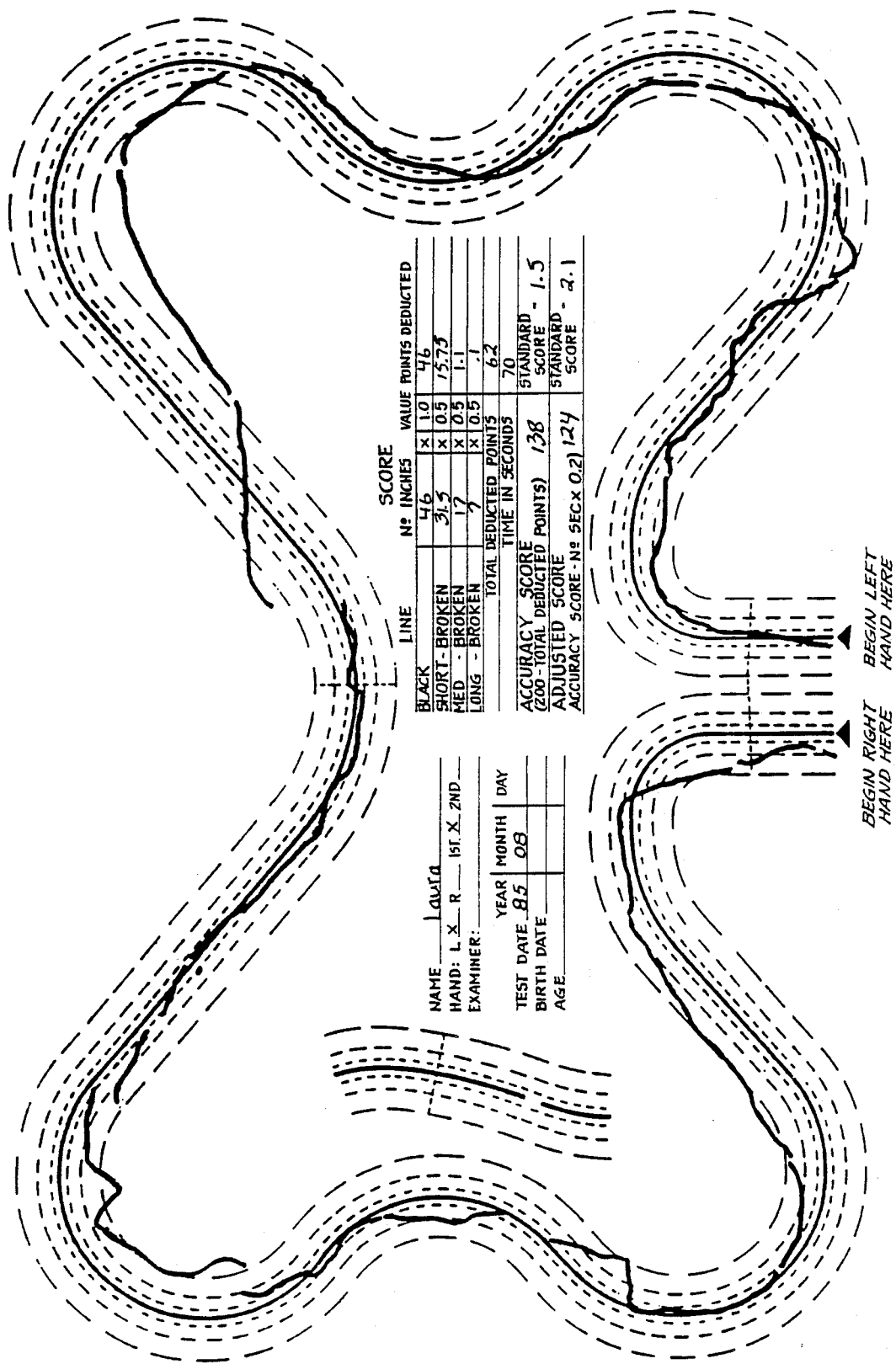

Each subject received the following evaluative procedures before implementing the experimental condition:
(1) Jebson Hand Function Test—A standardized test instrument designed to evaluate the quality and quantity of hand function skills in seven areas of medium and fine motor skills. The skills tested simulate common daily living tasks.
(2) Motor Accuracy Test—A standardized test instrument designed to evaluate the quality of paper and pencil type activities. (see, for example, FIGS. 12 and 14, wherein the subjects' motor accuracy skills, i.e., of duplicating the continuous line from the beginning point shown to the end point shown, were evaluated before implementing the experimental condition)
(3) Design Copying Test—A standardized test instrument used to evaluate eye-hand coordination and spatial perception. (see, for example, FIGS. 8 and 10, wherein the subjects' design copying skills, i.e., of copying the lines connecting the dots to form a design, were evaluated before implementing the experimental condition)

(4) Activities of Daily Living Timed Tests—A nonstandardized measure of speed required to don a loose fitting button down shirt and loose fitting shorts.

(5) Plumbline Test—A non-standardized measure of deviation frm midline occurring at the head, neck, and trunk during sitting activities.

Figure 9:
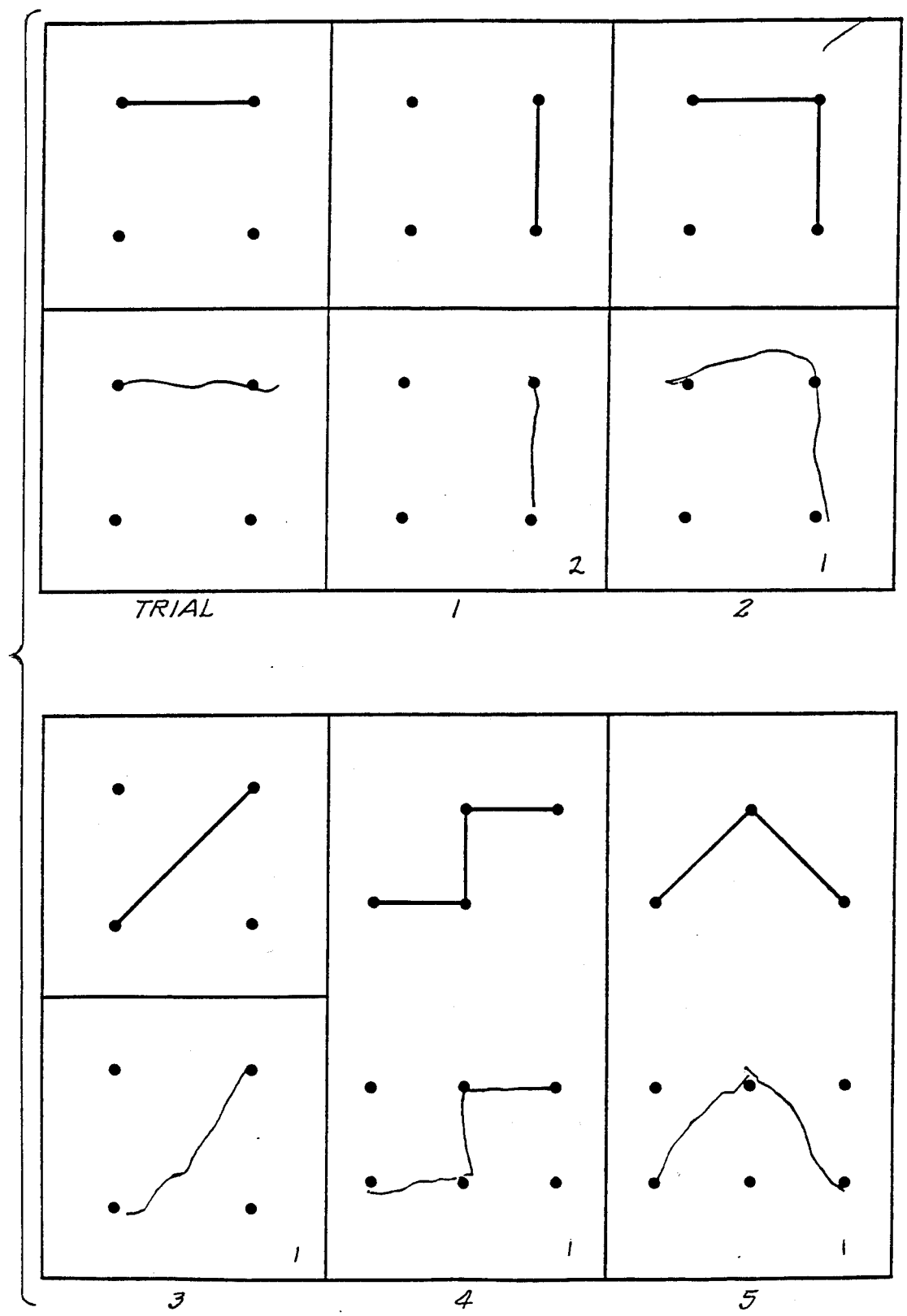
Figure 11:
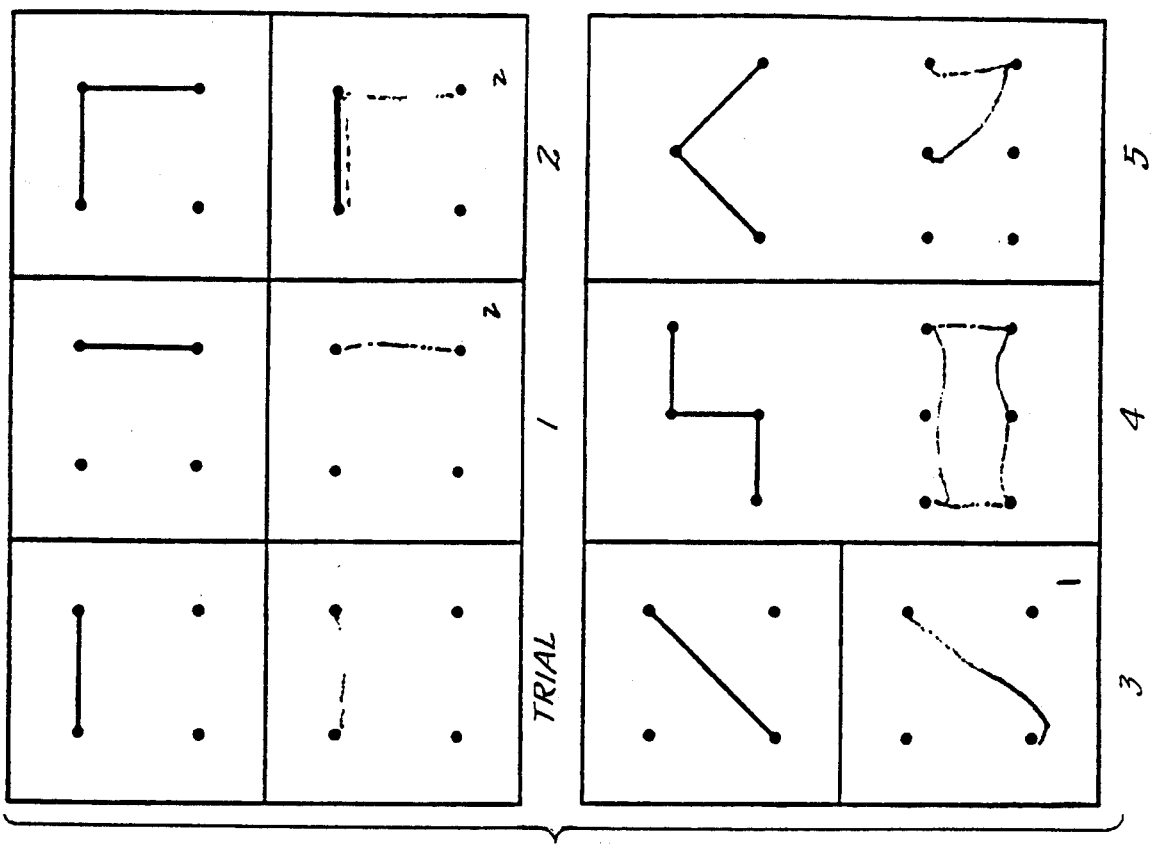
Figure 13:
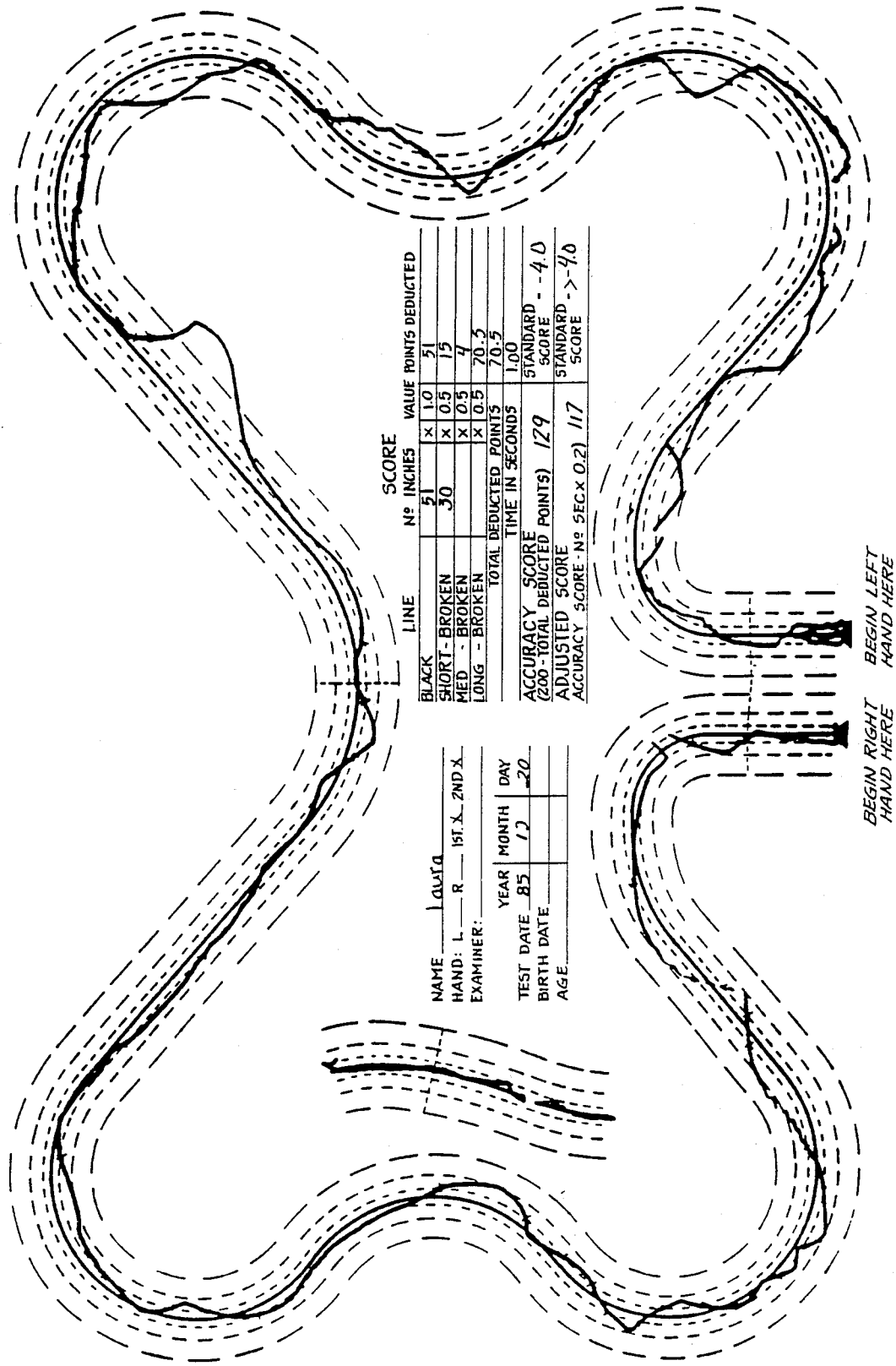
Figure 15:
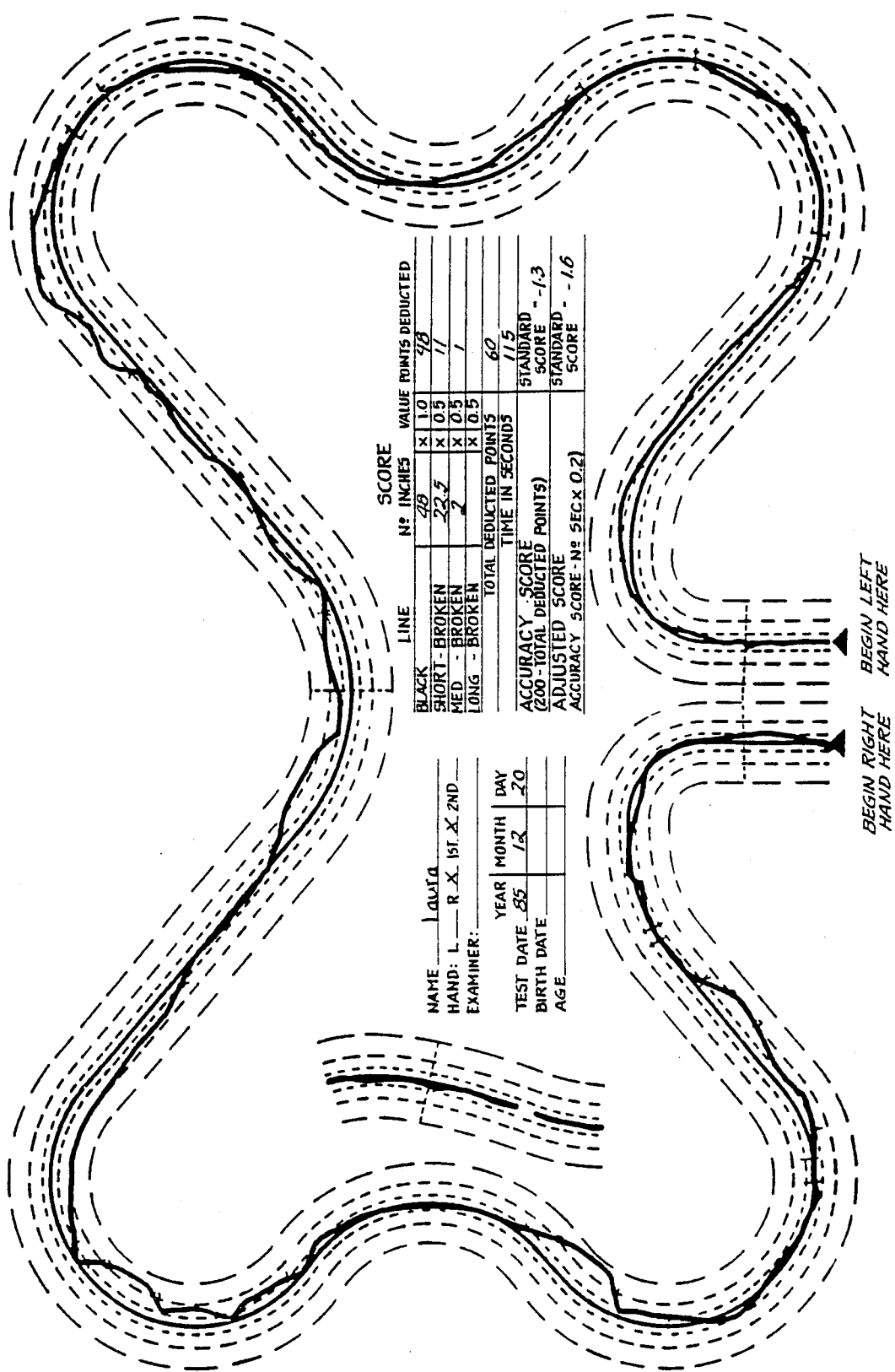

Each subject was re-evaluated with the same test instruments (these tests are reported to have good test-retest reliability) upon completion of the eight week experimental period. (see, e.g., FIGS. 9 and 11 for the results of the design copying tests and FIGS. 13 and 15 for the results of the motor accuracy tests) Each subject received treatment as prescribed by his physician, with the exception of those in group #1.

Treatment in Physical Therapy included exercises to increase developmental mobility. Treatment in Occupational Therapy included functional activities to increase bilateral use of the paper extremities, visual guidance of hand function tasks, joint mobility, selectivity in patterns of prehension, etc.

The results of this experiment showed that:

(a) Students who had experienced moderate graphomotor difficulties due to Minimal Cerebral Dysfunction (MCD) (Learning Disabilities) improved to within normal limits in twelve weeks with use of the NTM and Occupational Therapy and/or recommended therapeutic activities. This rate of improvement must be compared to the standard of 12 to 18 months normally anticipated with conventional treatment alone.

(b) Students who had experienced moderate difficulties in visuospatial orientation due to Minimal Cerebral Dysfunction (MCD) (Learning Disabilities) improved to within normal limits in twelve weeks given use of the NTM and Occupational Therapy and/or therapeutic home activities.

(c) Most of the students in this study experienced severe deficits in fine motor coordination. While all students showed significant improvement, only those using the NTM showed improvement to within normal limits in use of lateral prehension during the 12 weeks of the study. None of the students were able to achieve improvement to within normal limits in the Simulated Feeding Test.

(d) Cerebral Palsied students with severe spastic and visual perceptual involvement also showed significant gains in visuospatial orientation.

(e) Cerebral Palsied students with moderate spasticity in their dominant upper extremity were able to improve graphomotor skills to within normal limits in that extremity within 12 weeks, given NTM and a home program of therapeutic activities.

Thus, all students using the NTM showed significant improvement. Only students receiving Occupational Therapy and NTM showed overall improvement. Other students showed significant improvement, but only in certain areas of function.

The rate and degree of improvement was startling. Overall gains to within normal limits in treatment of children with MCD(LD) usually takes 12 to 18 months of treatment to achieve.

The significant gains in the area of Design Copying with the Cerebral Palsied students is extremely impressive. Such changes indicate that use of the NTM (not necessarily in conjunction with Occupational Therapy, but with specified activities to be completed in the home) alters the perceptual basis of body scheme, eye hand coordination, and visuospatial orientation in a measurable way.

The improvement gained with the Spastic Quadriplegic Cerebral Palsied in areas of visuospatial perception and fine motor coordination may have special implications for therapists and educators providing remedial services for the moderately to severely physically handicapped Cerebral Palsied child. Because these skills involve simultaneous integration and processing of sensory-motor and perceptual data, any significant improvement in these skills would necessarily indicate improvement in attention, organization, cognitive processing skills, and other neuropsychological parameters. Given the extent of improvement shown in the integrated task of Design Copying, in a relatively short period of time, one must question the effect of these treatment modalities upon the higher cortical functions of reading comprehension and math, which are known to be dependent upon visuospatial organization and other perceptual skills.

Item numbers 1 and 2 on the data sheets represent functional dexterity. It should be possible to correlate the scores by looking at unilateral versus bilateral results on both test items. Item number 3 can be viewed in isolation, or compared with scores on item number 4.

The above-described arrangement and methodology are merely illustrative of the principles of the present invention. Numerous modifications and adaptations thereof will be readily apparent to those skilled in the art without departing from the spirit and scope of the present invention.

TABLE 1

MALDEN GROSS MOTOR RATING SCALE I:
Cerebral Palsy Assessment

| Rating Points* | If the child can: | Then work on: | Age Level |
|---|---|---|---|
| 0 | Lie still in supine, reflex position | Getting head to midline | 1 month |
| 2.0 | Achieve midline in supine | Head control in prone | 2 months |
| 3.0 | Achieve head control in prone | Rolling from abdomen to back | 3 months |
| 4.0 | Roll from abdomen to back | Rolling from back to back | 4 months |
| 4.0 | Roll from back to abdomen | Pivoting, prone position | 4 months |
| 4.5 | Pivot, prone position | "Commando" creeping | 4–5 months |
| 5.0 | "Commando" creep | Primitive sitting | 5 months |
| 6.0 | Primitive sit | Sit with side protection | 6 months |
| 6.5 | Sit with side protection | Side-sitting when placed | 6–7 months |
| 8.0 | Side-sit when placed | Quadruped position; rock | 8 months |
| 8.5 | Maintain quadruped position; rock | Quadruped crawl | 8–9 months |
| 10.0 | Quadruped crawl | Assuming sitting from side-lying and quadruped | 9 months |
| 2.5 | Assume sitting | Kneel-standing | 10 months |
| 1.5 | Kneel-stand | Kneel-walking | 10–11 months |
| 2.0 | Kneel-walk | ½ kneel-stand | 11 months |
| 2.5 | ½ kneel-stand | Bipedal standing | 11–12 months |
| 70.0 points | | | |

*If the child is able to perform the activity in a normal manner, check the appropriate number. If his performance is less than normal, place an R next to the number or circle in red. If body integration is just beginning, place a Y next to the number or circle in yellow.

TABLE 2

MALDEN GROSS MOTOR RATING SCALE II:
(Bipedal stand through ambulation without supportive equipment)

| Rating Points* | If the child can: | Then work on: | Age Level |
|---|---|---|---|
| 10.0 | Bipedal stand | Side to side transfer of weight | 12 months |
| 1.0 | Transfer weight | Cruising to one side | 12 months |
| 1.5 | Cruise to one side | Cruising to the other side | 12 months |
| 1.5 | Cruise to both sides | 'Let go' between furniture for 1 or 2 steps | 12–14 months |
| 3.0 | 'Let go' for 1 or 2 steps | Get to stand with no assistance | 13–15 months |
| 3.0 | Get to stand with no assistance | Independent ambulation | 12–15 months |
| 10.0 | Independently walk | Advanced Gross motor activities | 12–48 months |
| 30.0 points | | | |

*If the child is able to perform the activity in a normal manner, check the appropriate number. If his performance is less than normal, place an R next to the number or circle in red. If body integration is just beginning, place a Y next to the number or circle in yellow.

TABLE 3

MALDEN GROSS MOTOR RATING SCALE III:
Cerebral Palsy Assessment
(Bipedal stand through ambulation with supportive equipment)

| Rating Points* | If the child can: | Then work on: | Age Level** |
|---|---|---|---|
| 10.0 | Bipedal stand | Side to side transfer of weight; use of rolling walker | 12 months |
| 1.0 | Ambulate with rolling walker | Ambulation-stationary walker | 15 months plus |
| 1.5 | Ambulate with stationary walker | Ambulation-cuffed crutches | 24 months plus |
| 1.5 | Ambulate with cuffed crutches | Ambulation-one crutch | 30 months plus |
| 2.0 | Ambulate with one crutch | Ambulation-2 canes | 36 months |
| 1.0 | Ambulate with two canes | Ambulation-1 cane | 40 months |
| 3.0 | Ambulate with one cane | Independent ambulation, if possible | 42 months |
| 10.0 | Independently ambulate | Balance and equilibrium | 48 months plus |
| 30.0 points | | | |

*If the child is able to perform the activity in a normal manner, check the appropriate number. If his performance is less than normal, place an R next to the number or circle in red. If body integration is just beginning, place a Y next to the number or circle in yellow.

**This is the average age level of accomplishment of the activity based on 25 years of pediatric private practice patients who had at least normal intelligence; fifty patients seen, seventy treatment sessions per week. Allowances should be made for the mentally retarded and patients who are incapable of accomplishing more difficult activities, although for the purposes of grading, the rating scale is effective.

TABLE 4

MALDEN GROSS MOTOR RATING SCALE IV

| Rating Points | Letter Rating* | Skill | Age Level |
|---|---|---|---|
| 2 | A | Stair climbing up, one step at a time, 2 feet on step | 2 years |
| 2 | B | Stair climbing down, one step at a time with 2 feet on step | 2 years |
| 3 | C | Stair climbing up, foot over foot, alternating with 1 foot on each step | 3 years |
| 3 | D | Stair climbing down, foot over foot, alternating with 1 foot on each step | 3 years |
| 2 | E | Running* | 2 years |
| 2 | F | Jumping with both feet simultaneously | 2 years |
| 2.5 | G | Standing on one foot | 3–4 years |
| 2.5 | H | Standing on other foot** | 3–4 years |
| 5 | I | Hopping on one foot | 3–4 years |
| 5 | J | Hopping on other foot** | 3–4 years |
| 50 | K | Skipping (highest gross motor independent skill | 5.5 years |
| 2.5 | L | Standing on one foot with eyes closed | 6 years |
| 2.5 | M | Standing on other foot** with eyes closed | 6 years |
| 5 | N | Riding tricycle or bicycle with training wheels | 3–4 years |
| 11 | O | Riding bicycle | 4–5 years |
| 100 points | | | |

*Letter value used to detail gross motor skills.
**If hemiplegia is present, comment on quality with R or Y as on previous scales.

TABLE 5

SPASTIC CEREBRAL PALSY CAPABILITY ANALYSIS
Active Treatment - First six weeks - GROUP A
Values from a total of 200 possible points (Scales I–IV)

| Patient Number | Original Assessment | Period of months of therapy prior to study | Assessment Start of study | Assessment at Crossover between active and placebo | Assessment At end of study |
|---|---|---|---|---|---|
| 1 | 82.0 | 18 mos. | 126.5 | 184.0 | 184.0 |
| 2 | 0 | 26 mos. | 4.5 | 7.0 | 9.5 |
| 7 | 0 | 12 mos. | 2.0 | 7.5 | 9.5 |
| 9 | 0 | 3 mos. | 0.0 | 2.0 | 2.5 |
| 11 | 114.0 | 17 mos. | 132.5 | 195.0 | 200.0 |
| 12 | 44.0 | 9 mos. | 51.5 | 60.0 | 60.0 |
| 13 | 0.5 | 6 mos. | 4.0 | 15.0 | 19.0 |
| 14 | 10.0 | 21 mos. | 51.0 | 105.0 | 107.0 |
| 15 | 21.5 | 8 mos. | 51.0 | 102.0 | 102.0 |
| 20 | 100.0 | 11 mos. | 106.0 | 116.5 | 116.5 |
| Average | 37.2 | 13.1 mos. | 52.9 | 79.4 | 81 |

TABLE 6

SPASTIC CEREBRAL PALSY CAPABILITY ANALYSIS
Placebo Treatment - First six weeks - GROUP B
Values from a total of 200 possible points (Scales I-IV)

| Patient Number | Original Assessment | Period of months of therapy prior to study | Assessment Start of study | Assessment at Crossover between active and placebo | Assessment At end of study |
|---|---|---|---|---|---|
| 3 | 70.5 | 41 mos. | 107.0 | 107.0 | 129.0 |
| 4 | 14.5 | 14 mos. | 55.0 | 55.0 | 62.0 |
| 6 | 55.5 | 14 mos. | 104.0 | 104.0 | 108.0 |
| 10 | 21.5 | 13 mos. | 55.5 | 65.5 | 104.0 |
| 19 | 49.0 | 54 mos. | 110.0 | 114.0 | 119.0 |
| 5 | 2.0 | .5 mos. | 2.0 | Discontinued (Adopted as normal) after 2 active treatments | |
| 17 | 10.0 | 87 mos. | 80.0 | 82.0 | 90.0 |
| 8 | Discontinued due to illness. | | | | |
| 16 | Discontinued due to parent's illness. | | | | |
| 18 | Discontinued due to orthopedic surgery. | | | | |
| Average | 36.83 | 37.16 | 85.4 | 87.9 | 102 |

What is claimed is:

1. A method for suppressing pain and reducing spasticity associated with cerebral palsy including the steps of respectively securing electrodes transcranially to the right and left side of a patient's head, a first electrode being secured to the right side and a second electrode to the left side, and applying a high frequency electrical wave bearing a low frequency amplitude modulation to said first and said second electrodes.

2. The method of claim 1, in which said first and second electrodes are respectively placed between the ear and temple on left and right sides of the patient's head.

3. The method as in claim 1, wherein the frequency of said high frequency electrical wave is in the range of 12-20 khz, wherein said low frequency modulation is in the range 8-20 hz, and wherein said wave is less than 4 milliamperes.

4. The method as in claim 3, wherein said amplitude modulation is non-symmetrical.

* * * * *